United States Patent [19]
Ritz et al.

[11] Patent Number: 5,914,330
[45] Date of Patent: Jun. 22, 1999

[54] NEPHROPROTECTIVE PHARMACEUTICAL COMPOSITION AND USE THEREOF

[75] Inventors: Eberhard Ritz; Kerstin Amann, both of Heidelberg; Gerhard Wilhelm Bielenberg, Alfeld/Leine, all of Germany

[73] Assignee: Solvay Pharmaceuticals GmbH, Hannover, Germany

[21] Appl. No.: 09/084,916

[22] Filed: May 28, 1998

[30] Foreign Application Priority Data

May 28, 1997 [DE] Germany .................. 197 22 322

[51] Int. Cl.$^6$ .................................................. A61K 31/505
[52] U.S. Cl. ............................................................ 514/269
[58] Field of Search ................................................ 514/269

[56] References Cited

U.S. PATENT DOCUMENTS 4,323,570  4/1982  Stenzel et al. ........................ 424/251
5,712,283  1/1998  Kaan et al. ............................ 514/269

*Primary Examiner*—Raymond Henley, III
*Attorney, Agent, or Firm*—Evenson, McKeown, Edwards & Lenahan, P.L.L.C

[57] ABSTRACT

The use of sub-antihypertensive doses of moxonidine or a physiologically compatible acid addition salt thereof for inhibiting renal failure, independent of a reduction in blood pressure, and/or for the preparation of pharmaceutical preparations for the treatment and/or prophylaxis, independent of a reduction in blood pressure, of renal failure.

6 Claims, No Drawings

NEPHROPROTECTIVE PHARMACEUTICAL COMPOSITION AND USE THEREOF

BACKGROUND OF THE INVENTION

The present invention relates to the use of 4-chloro-5-[(4,5-dihydro1H-imidazol-2-yl)-amino]-6-methoxy-2-methyl-pyrimidine (=moxonidine) and the physiologically compatible acid addition salts thereof for the treatment and/or prophylaxis of renal failure in normotensive patients; to the preparation of medicaments suitable for this treatment, and to pharmaceutical compositions for effecting such a treatment.

SUMMARY OF THE INVENTION

It is an object of the invention to provide a new method of treating renal failure.

It is also an object of the invention to provide a method of preparing new pharmaceutical preparations for the treatment of renal failure in normotensive patients.

An additional object of the invention is to provide new nephroprotective pharmaceutical compositions containing sub-antihypertensive amounts of moxonidine.

These and other objects have been achieved in accordance with the present invention by providing a method of treating renal failure comprising the step of administering to a patient in need of such treatment 4-chloro-5-[(4,5-dihydro1H-imidazol-2-yl)-amino]-6-methoxy-2-methylpyrimidine corresponding to Formula I

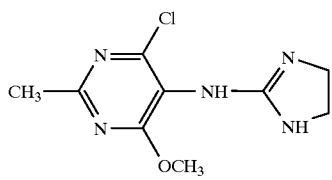

or a physiologically acceptable acid addition salt thereof in an amount effective to inhibit renal failure but insufficient to produce a reduction in blood pressure.

In accordance with a further aspect of the invention, the objects have been achieved by providing a method of preparing a pharmaceutical composition for treatment of renal failure independent of a reduction in blood pressure, which method comprises incorporating a sub-antihypertensive, nephroprotective amount of 4-chloro-5-[(4,5-dihydro1H-imidazol-2-yl)-amino]-6-methoxy-2-methylpyrimidine corresponding to Formula I

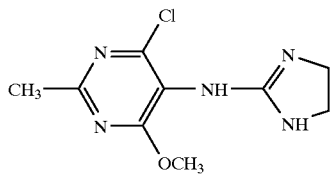

or a physiologically acceptable addition salt thereof and at least one pharmaceutical carrier or adjuvant into a pharmaceutical dosage form.

According to yet another aspect of the invention, the objects are achieved by providing a pharmaceutical composition for treatment of renal failure independent of a reduction in blood pressure, which composition comprises a pharmaceutical dosage form comprising a sub-antihypertensive, nephroprotective amount of 4-chloro-5-[(4,5-dihydro1H-imidazol-2-yl)-amino]-6-methoxy-2-methyl-pyrimidine corresponding to Formula I

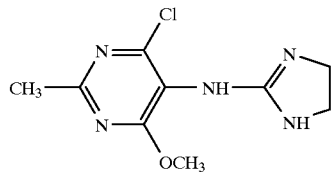

or a physiologically acceptable addition salt thereof and at least one pharmaceutical carrier or adjuvant.

DETAILED DESCRIPTION OF PREFERRED EMBODIMENTS

According to the invention, 4-chloro-5-[(4,5-dihydro-1H-imidazol-2-yl)-amino]-6-methoxy-2-methylpyrimidine of Formula I

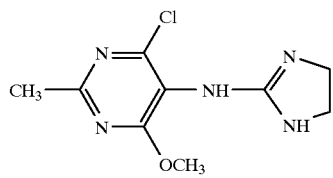

and the physiologically compatible acid addition salts thereof are used for the preparation of pharmaceutical preparations for the treatment, independent of a reduction in blood pressure, of renal failure, e.g. in normotensive patients.

Suitable physiologically acceptable acid addition salts of moxonidine include salts with inorganic acids, for example hydrohalic acids, or with organic acids, for example lower aliphatic monocarboxylic or dicarboxylic acids, such as acetic acid, fumaric acid or tartaric acid, or aromatic carboxylic acids such as salicylic acid.

The compounds used according to the invention for the treatment, independent of a reduction in blood pressure, of renal failure fall within the scope of 5-[(2-imidazolin-2-yl)-amino]-pyrimidine derivatives having hypotensive properties described in German Offenlegungsschrift No. 28 49 537, and are known from this patent application. Pharmaceutical preparations which contain moxonidine are commercially available as antihypertensive agents under the trade name Physiotens™, and are medicinally used as antihypertensive agents. The compounds may be prepared in known manner according to the methods described in the above Offenlegungsschrift, or analogously to these methods.

It is known that there are interactions between high blood pressure and chronic renal failure, in that firstly high blood pressure places great stress on the kidneys and may result in damage to kidney function, and secondly that chronically reduced kidney function often results in high blood pressure. It is furthermore known from a study by Mall et al (Cardiovascular Risk Factors Vol. 5, Suppl. 1, 1995, pages 33–39) that a reduction in blood pressure (e.g. by administering hypotensive pharmaceutical active substances, inter alia moxonidine) has a nephroprotective effect and can alleviate or prevent kidney damage.

Surprisingly, it has now been discovered that moxonidine and its physiologically compatible acid addition salts have a nephroprotective action on humans and larger mammals even in sub-antihypertensive doses, and result in the slowing or inhibition of the progression of reduced kidney performance. Thus moxonidine is also suitable for the prophylaxis and treatment, independent of a reduction in blood pressure, of kidney damage and renal failure, e.g. in normotensive patients. Those doses which do not cause any physiologically relevant reduction in blood pressure are referred to as sub-antihypertensive doses within the scope of the present invention. Those patients who are either spontaneously normotensive or are rendered normotensive by taking other hypotensive agents are referred to as normotensive within the scope of the present invention. According to the invention, a treatment with moxonidine which is essentially free of reduction in blood pressure (i.e. treatment with doses which do not cause any physiologically or pharmacologically significant reduction in blood pressure) is used to prevent or alleviate kidney disease, and can promote renormalisation of damaged kidney structure.

Moxoni dine and its physiologically acceptable acid addition salts may be administered in conventional pharmaceutical preparations, orally, intravenously or alternatively transdermally for the treatment of renal failure according to the invention.

Thus, sub-antihypertensive nephroprotective quantities of the compounds may be contained according to the invention, together with conventional pharmaceutical auxiliaries' and/ or carriers, in solid or liquid pharmaceutical preparations. Examples of solid preparations include preparations which can be administered orally, such as tablets, coated tablets, capsules, powders or granules, or alternatively suppositories. These solid preparations may contain conventional pharmaceutical inorganic and/or organic carriers, e.g. lactose, talcum or starch, in addition to conventional pharmaceutical auxiliaries, for example lubricants or tablet disintegrating agents. Liquid preparations such as solutions, suspensions or emulsions of the active substances may contain the usual diluents such as water, oils and/or suspension agents such as polyethylene glycols and the like. Other auxiliaries or adjuvants may additionally be added, such as preservatives, taste correctives and the like.

The active substances may be mixed and formulated with the pharmaceutical auxiliaries and/or carriers in known manner. For the production of solid medicament forms, the active substances may for example be mixed with the auxiliaries and/or carriers in conventional manner and may be granulated in the wet or dry state. The granules or powder may be poured directly into capsules or be pressed into tablet cores in conventional manner. These may be coated in known manner if desired.

The nephroprotective action of moxonidine in the sub-antihypertensive dose range was demonstrated in standard animal tests on rats.

According to the invention, doses in a range in which no pharmacologically relevant hypotensive effects occur in the species being treated are used as sub-antihypertensive doses. In order to investigate the influence of sub-antihypertensive doses of moxonidine on the progression of renal failure, the animal model of the subtotally nephrectomised rat which is known as a test model for kidney damage was used. Therein, the glomerulosclerosis index was determined as the generally accepted surrogate marker for the degree of kidney damage or reduction in kidney performance which occurs.

DESCRIPTION OF THE PHARMACOLOGICAL TESTS

Male Sprague-Dawley rats were fed a diet containing 40 g protein and 0.6 g NaCl per 100 g. After a 7-day adaptation phase, a subtotal nephrectomy was performed. Therein, in a first operation a nephrectomy was performed on the right kidney under short-term anaesthesia (ketamine/xylazine i.m.) by clamping off and ligating the renal artery and displacing the renal capsule in order to obtain the suprarenal gland. After 5 days, at a time at which compensatory hypertrophy of the left kidney had occurred, in a second operation under anaesthesia (ketamine/xylazine i.m.) a resection of the upper and lower pole of the left kidney was performed. From the third day after the second operation onwards, a group of 10 animals was administered moxonidine p.o. in a daily dose of approximately 1.5 mg/kg via the feed pellets for the entire investigation period of 12 weeks. A control group of animals was given the same diet without moxonidine, with a paired feeding protocol ensuring that treated and untreated animals had the same quantity of food. Permanent monitoring of blood pressure was carried out for some of the test animals (4 animals per test group). The blood pressure parameter was detected with the aid of telemetric data transmission (Data Sciences International, St. Paul. Minn., USA). To this end, the rats had a pressure catheter connected to a transmitter implanted in the abdominal aorta.

At the end of the test, the kidneys were prepared under anaesthesia (ketamine/xylazine i.m) using quantitative stereological methods after perfusion fixation. To this end, a catheter was introduced into the abdominal aorta. The vascular system was fixed at a perfusion pressure of 110 mm Hg by means of this catheter after washing out with a dextran solution (Rheomakrodex; Schiwa Co., Glandorf) for 12 minutes with a 0.2 molar phosphate buffer which contained 3% glutaric dialdehyde. The kidneys were weighed, and cut into slices 1 mm thick. The slices were embedded in paraffin, cuts 4 $\mu$m thick were made and were stained with haematoxylin/eosin. The glomerulosclerosis index was determined using light microscopy according to the method of Raij et al (Raij L., Azar S., Keane W. Kidney Int. 1984; 26: 137–143). In so doing, in at least 1000 glomeruli the sclerosis was classified according to the surfaces affected into degrees of severity of 0 to 4 (0=no damage; 1=up to 25%; 2=25 to 50%; 3=50 to 75%; 4=75 to 100%).

The test results are reproduced in the following table. The values of the glomerulosclerosis index given in the table are mean values +/− standard deviation of the measurement on 10 animals in each case. The blood pressure values are mean values +/− standard deviation of the blood pressure measurement, determined by telemetry, on 4 animals in each case. The pressure values are given as mean systolic blood pressure over 24 hours in each case in the first to ninth weeks of treatment.

TABLE

| Test group | Glomerulo-sclerosis index | Systolic blood pressure (mm Hg) after | |
|---|---|---|---|
| | | 1 week's treatment | 9 weeks' treatment |
| Control | 1.55 ± 0.28 | 136.6 ± 5.9 | 131.3 ± 5.3 |
| Moxonidine | 0.89 ± 0.10* | 135.9 ± 2.1 | 140.6 ± 7.0 |

*= p <0.05 (t-Test)

The above test results show that with moxonidine treatment for blood pressure values which are approximately constant the glomerulosclerosis index is reduced by more than 40%. This is an indication of the inhibiting effect of the moxonidine on the progression of reduction of the kidney performance and of kidney damage.

For this reason, moxonidine and its acid addition salts are suitable for the prophylaxis and treatment, independent of a reduction in blood pressure, of renal failure. The doses to be used may vary individually and will naturally vary according to the type of condition to be treated and the form of administration. In general, however, medicinal forms with an active substance content of 0.05 to 0.2 mg per individual dose are suitable for oral administration to larger mammals, in particular humans.

The following example is intended to illustrate in greater detail the preparation of a moxonidine-containing pharmaceutical composition which is suitable for the treatment of renal failure, without however restricting the scope of the invention.

EXAMPLE 1

Moxonidine-containing film-coated tablets.

| Composition: | | |
|---|---|---|
| Tablet cores: | | |
| Moxonidine | 0.010 | parts |
| Lactose | 9.590 | parts |
| Povidone USP | 0.070 | parts |
| Crospovidone USP | 0.300 | parts |
| Magnesium stearate | 0.030 | parts |
| (Water | 0.750 | parts) |
| Total solids | 10,000 | parts |
| Film coating: | | |
| Hydroxypropyl methyl cellulose | 0.156 | parts |
| 30% aqueous ethyl cellulose dispersion | 0.480 | parts |
| (≈ solids) | (0.144) | parts |
| Polyethylene glycol 6000 | 0.030 | parts |
| Titanium dioxide | 0.150 | parts |
| Talcum | 0.1197 | parts |
| Red iron oxide | 0.0003 | parts |
| (Water | 3.864 | parts) |
| Total solids | 0.600 | parts |
| Total quantity film coating suspension | 4,800 | parts |

4.8 kg of the above film coating suspension were used for coating 10,000 tablet cores of a weight of 100 mg each.

Production of tablet cores

The moxonidine and the lactose were mixed. The mixture was moistened thoroughly with a solution of the binder Povidone in water, was kneaded thoroughly and the resulting product was spread out on trays and dried to a moisture content of at most 0.5% at a temperature of approximately 50° C. The dried product was passed through a 0.75 mm sieve (Frewitt machine). Once the resulting granules had been mixed with crospovidone and magnesium stearate, tablet cores having a weight of 100 mg were pressed therefrom, so that each tablet core contained 0.1 mg active substance.

Preparation of the film coating suspension

The hydroxypropyl methyl cellulose and the polyethylene glycol 6000 were dissolved in part of the water. A suspension of talcum, titanium dioxide and iron oxide in the rest of the water was added to this solution with stirring. The resulting suspension was diluted with the 30% aqueous ethyl cellulose dispersion with slight stirring.

Film coating of the tablet cores

The film coating suspension was sprayed on to the tablet cores in a film-coating apparatus, while hot air at about 70° C. heated the tablet cores to a temperature of about 45°C. Then the film-coated tablets were dried for 16 hours at a temperature of approximately 45° C.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method of treating renal failure comprising the step of administering to a patient in need of such treatment 4-chloro-5-[(4,5-dihydro1H-imidazol-2-yl)-amino]-6-methoxy-2-methylpyrimidine corresponding to Formula I

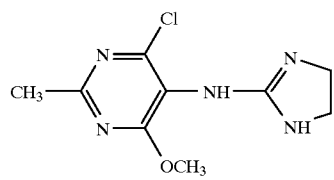

or a physiologically acceptable acid addition salt thereof in an amount effective to inhibit renal failure but insufficient to produce a reduction in blood pressure.

2. A method according to claim 1, wherein said 4-chloro-5-[(4,5-dihydro1H-imidazol-2-yl)-amino]-6-methoxy-2-methylpyrimidine is administered orally in a dosage form having an active substance content of from 0.05 to 0.2 mg per individual dose.

3. A method of preparing a pharmaceutical composition for treatment of renal failure independent of a reduction in blood pressure, said method comprising incorporating a sub-antihypertensive, nephroprotective amount less than 0.2 mg of 4-chloro-5-[(4,5-dihydro1H-imidazol-2-yl)-amino]-6-methoxy-2-methylpyrimidine corresponding to Formula I

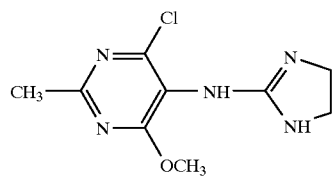

or a physiologically acceptable addition salt thereof and at least one pharmaceutical carrier or adjuvant into a pharmaceutical dosage form.

4. A method according to claim 3, wherein said pharmaceutical dosage form is an orally administrable dosage form having an active substance content of from 0.05 to less than 0.2 mg per individual dose.

5. A pharmaceutical composition for treatment of renal failure independent of a reduction in blood pressure, said composition comprising a pharmaceutical dosage form comprising a sub-antihypertensive, nephroprotective amount less than 0.2 mg of 4-chloro-5-[(4,5-dihydro1H-imidazol-2-yl)-amino]-6-methoxy-2-methylpyrimidine corresponding to Formula I

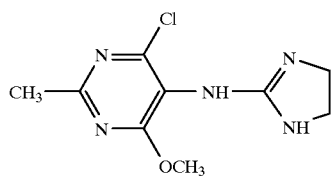
or a physiologically acceptable addition salt thereof and at least one pharmaceutical carrier or adjuvant.
6. A pharmaceutical composition according to claim 5, wherein said pharmaceutical dosage form is an orally administrable dosage form having an active substance content of from 0.05 to less than 0.2 mg per individual dose.
* * * * *